United States Patent
Feng et al.

(10) Patent No.: US 11,247,977 B2
(45) Date of Patent: Feb. 15, 2022

(54) COMPOUND AND USE THEREOF IN SYNTHESIS OF BRIVARACETAM INTERMEDIATE AND CRUDE DRUG

(71) Applicant: FUJIAN HAIXI PHARMACEUTICALS CO., LTD, Fujian (CN)

(72) Inventors: Yan Feng, Fujian (CN); Ruyong Wang, Fujian (CN); Yizhang Ye, Fujian (CN); Fengsen Zhang, Fujian (CN); Xuan Gong, Fujian (CN); Zhonghong Wang, Fujian (CN); Xinshan Kang, Beijing (CN)

(73) Assignee: FUJIAN HAIXI PHARMACEUTICALS CO., LTD., Fujian (CN)

( * ) Notice: Subject to any disclaimer, the term of this patent is extended or adjusted under 35 U.S.C. 154(b) by 0 days.

(21) Appl. No.: 17/253,135

(22) PCT Filed: Jun. 20, 2019

(86) PCT No.: PCT/CN2019/092105
§ 371 (c)(1),
(2) Date: Dec. 17, 2020

(87) PCT Pub. No.: WO2019/242692
PCT Pub. Date: Dec. 26, 2019

(65) Prior Publication Data
US 2021/0261515 A1    Aug. 26, 2021

(30) Foreign Application Priority Data
Jun. 22, 2018   (CN) .......................... 201810651559.9

(51) Int. Cl.
*C07D 307/33*     (2006.01)
*C07D 405/12*     (2006.01)

(52) U.S. Cl.
CPC ......... *C07D 307/33* (2013.01); *C07D 405/12* (2013.01); *C07B 2200/07* (2013.01)

(58) Field of Classification Search
CPC .................................................. C07D 307/33
See application file for complete search history.

(56) References Cited

FOREIGN PATENT DOCUMENTS

| | | | |
|---|---|---|---|
| CN | 105646319 A | 6/2016 |
| CN | 105801530 A | 7/2016 |
| CN | 105837535 A | 8/2016 |
| CN | 106008411 A | 10/2016 |
| CN | 106279074 A | 1/2017 |
| CN | 106432030 A | 2/2017 |
| CN | 107652254 A | 2/2018 |
| CN | 109134406 A | 1/2019 |
| WO | 2016191435 A1 | 12/2016 |
| WO | 2020/143674 A1 | 7/2020 |

OTHER PUBLICATIONS

Search Report dated Aug. 18, 2021 for European patent application No. 19821607.9.
Nakada Kazuaki et al., "Cyclopropane-based conformational restriction of GABA by a atereochemical diversity-oriented strategy: Identification of an efficient lead for potent inhibitors of GABA transports", Bioorganic & Medicinal Chemistry, Elsevier, Amsterdam, NL,vol. 21, No. 17, Jul. 8, 2013, pp. 4938-4950.
Konrádová Daniela et al:"1-(Phenylsulfonyl)-3-oxabicyclo[3.1 0]hexan-2-one as a Building Block in Organic Synthesis", The Journal of Organic Chemistry, vol. 83, No. 19, Oct. 5, 2018, pp. 12229-12238.
First Examination Report dated May 12, 2021 for Indian patent application No. 202117000063, 4 pages.
International Search Report for PCT/CN2019/092105 dated Aug. 28, 2019, ISA/CN.
Kazuta, Yuji, et al. Development of Versatile cis-and trans-Dicarbon-Substituted Chiral Cyclopropane Units: Synthesis of (1S, 2R)-and (1R,2R)-2-Aminomethyl-1-(1H-imidazol-4-yl) cyclopropanes and Their Enantiomers as Conformationally Restricted Analogues of Histamine, Journal of Organic Chemistry, vol. 67, No. (5), Feb. 1, 2002, ISSN:0022-3263, p. 1669-1677.
Rodriguez, Carmen M. et al. Stereoselective Synthesis of Highly SubstitutJ. Org. Chem. 1994,59,4461-4472ed γ-Lactones and Butenolides by Intramolecular Michael Addition of Enantiomerically Enriched γ-[(Phenylthio)acyl]oxy α,β-Unsaturated Esters, Journal of Organic Chemistry, vol. 59, No. (16), Dec. 31, 1994, ISSN:0022-3263, p. 4461-4472.

(Continued)

*Primary Examiner* — Golam M Shameem
(74) *Attorney, Agent, or Firm* — Yue (Robert) Xu; Apex Attorneys at Law, LLP

(57) ABSTRACT

The present application provides a compound in formula III, and further provides a use of the compound in the synthesis of a Brivaracetam intermediate and a crude drug, and a synthesis method. A raw material involved in the method of the present application is low in costs and easily available; (R)-4-propyl-dihydrofuran-2-ketone having high optical purity can be prepared; complicated separation and purification steps are avoided; costs are reduced, and the method is more applicable to industrial production.

(III)

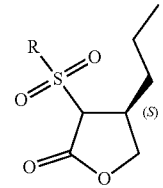

13 Claims, No Drawings

(56) References Cited

OTHER PUBLICATIONS

Jung, Beom Son. et al. Enantioselective Total Synthesis of (−)-Clavosolide A and B, Bull Korean Chern Soc., vol. 31, No. (3), Dec. 31, 2010, ISSN:0253-2964, p. 653-663.

Sylvie Robin, et al. Microbiological reduction of keto-sulfones. Application in a three-step synthesis of (S)-(+)-pβ-angelica lactone, Tetrahedron Asymmetry,vol. 4, No. (2), Dec. 31, 1993, ISSN:0957-4166, p. 239-246.

Arnaud Schule. et al. A bio-catalytic route to the novel anti-epileptic drug Brivaracetam, Org. Process Res. 2016, 20, p. 1566-1575.

COMPOUND AND USE THEREOF IN SYNTHESIS OF BRIVARACETAM INTERMEDIATE AND CRUDE DRUG

This application is the national phase of International Application No. PCT/CN2019/092105, titled "COMPOUND AND USE THEREOF IN SYNTHESIS OF BRIVARACETAM INTERMEDIATE AND CRUDE DRUG", filed on Jun. 20, 2019, which claims the priority of Chinese Patent Application No. 201810651559.9, titled "COMPOUND AND USE THEREOF IN SYNTHESIS OF BRIVARACETAM INTERMEDIATE AND CRUDE DRUG", filed on Jun. 22, 2018 with the China National Intellectual Property Administration, which is incorporated herein by reference in entirety.

FIELD OF THE INVENTION

The invention relates to the field of synthesis of pharmaceutical intermediates, in particular to a class of sulfonyl substituted compounds and their synthesis, and their applications in the synthesis of intermediates and APIs of Brivaracetam. The information provided is intended solely to assist the understanding of the reader. None of the information provided nor references cited is admitted to be prior art to the present invention. Each of the references cited is incorporated herein in its entirety and for any purpose.

BACKGROUND OF THE INVENTION

Brivaracetam belongs to the third generation antiepileptic drug and is a novel high-affinity ligand for synaptophysin 2A (SV2A), which also inhibits voltage-dependent sodium channels. In 2016, Brivaracetam was approved by the FDA for the treatment of seizures, and the results showed that Brivaracetam has a good effect on generalized seizures.

Many synthetic routes have been reported in the literature and patents of Brivaracetam, among which (R)-4-propyl-dihydrofuran-2-one is the most important chiral intermediate. After comprehensive review of the data, we found that there are several routes with industrialization value at present as follows:

WO 2016191435 and CN105646319 respectively disclose the use of inexpensive R-epichlorohydrin as a chiral source, which is reacted with malonic acid diester, and the resulting cyclopropyl compound is opened under the action of ethyl magnesium bromide, followed by decarboxylation to give (R)-4-propyl-dihydrofuran-2-one, the reaction route is as follows:

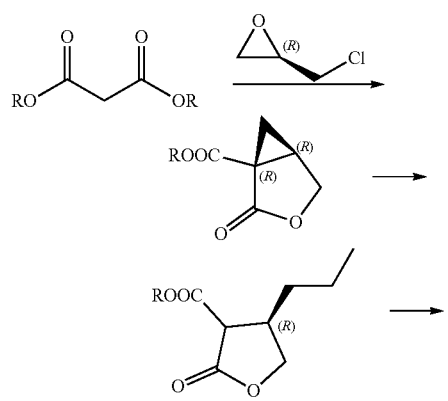

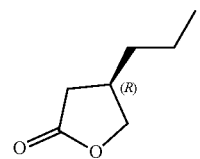

WO2016191435 disclose a method that uses diethyl malonate as raw material. Although the raw material is cheap and easy to obtain, it needs many times of vacuum distillation, which requires higher equipment requirements. CN105646319 disclose a method that uses diphenyl malonate as raw material. It overcomes the shortcoming of patent WO2016191435. The intermediate can be purified by crystallization and has ultraviolet absorption, which can be detected by HPLC, but the raw material cost is high.

CN105801530 disclose a method that uses R-2-aminopentanoic acid (D-n-valine) as starting material. Firstly, the amino group is transformed to bromine group by diazotization, then the carboxyl group is reduced to alcohols, which then reacted with diethyl malonate after being protected by silicon groups. Finally, (R)-4-propyl-dihydrofuran-2-one was obtained by decarboxylation and ring closed in acidic conditions. The route is as follows:

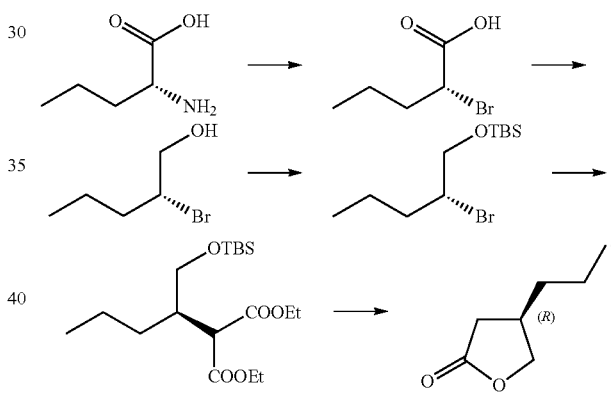

This route has been used for column chromatography many times, and R-2-aminopentanoic acid is not a natural amino acid, which is currently costly at present.

The literature [Org. Process Res. Dev. 2016, 20, 1566-1575] reports a method of enzymatic resolution, the route is as follows:

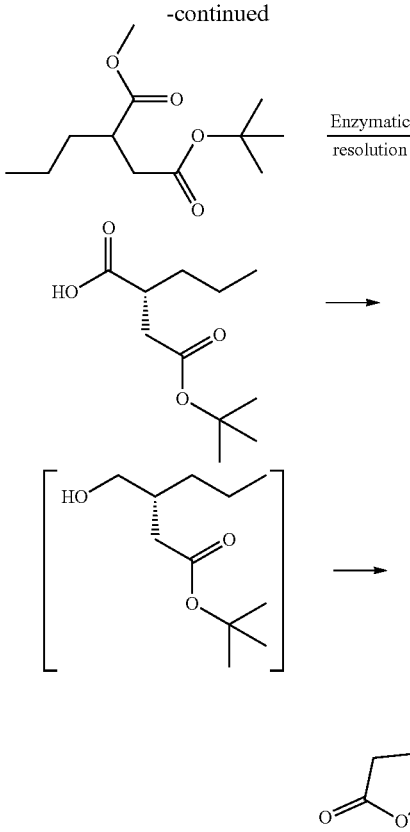

Although this method has a high yield of intermediates and does not require purification, the total yield of enzymatic resolution is not high and the current production capacity is small.

CN105837535 and CN106008411 respectively disclose a method for synthesizing (R)-4-propyl-dihydrofuran-2-one using chiral oxazolinone as a chiral auxiliary reagent, the route is as follows:

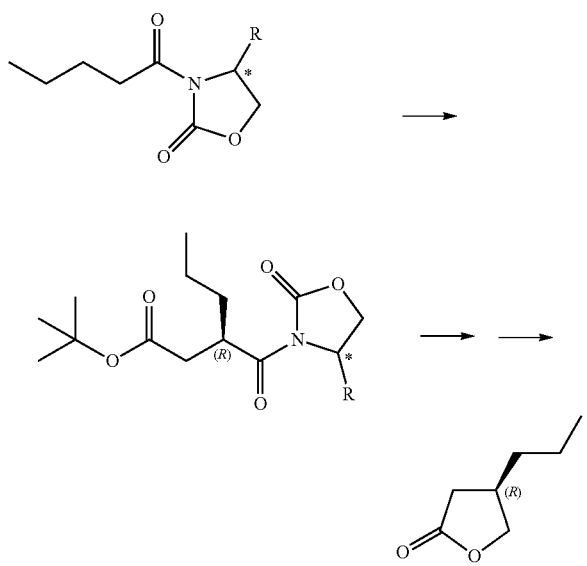

Ultra-low temperature reaction is needed in this route, which requires high equipment, and multi-step intermediates are oily substances, which can not be purified by crystallization or need be purified by column chromatography.

In view of the above known synthetic methods, most of the intermediates involved are liquid without ultraviolet absorption, which are difficult to purify, detect and quality control, or costly to synthesize, or require special equipment to complete the isomer separation and purification by column chromatography. So they are not suitable for large-scale industrial production. In order to overcome the problems in the reported routes, it is an object of the present invention to provide a process for the preparation of 3-sulfonyl-substituted 4-propyl-dihydrofuran-2-one, and their applications in the synthesis of intermediate (R)-4-propyl-dihydrofuran-2-one and APIs of Brivaracetam. This method has achieved creative breakthroughs. For example, its synthetic route is short, raw materials are easy to obtain, process is simple, the detection and quality control of intermediates is simple and easy. Compared with the existing synthetic process, it has obvious cost advantages and process advantages, and is very suitable for the industrial production of Brivaracetam APIs.

The present invention provides a compound of formula III which is useful in the preparation of Brivaracetam API.

A compound having the structure of formula III:

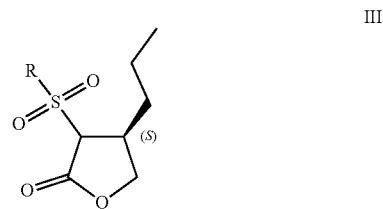

III

Wherein, R is selected from optionally substituted or unsubstituted $C_1$-$C_5$ alkyl, optionally substituted or unsubstituted $C_6$-$C_{12}$ Aryl, optionally substituted or unsubstituted 5-12 membered heteroaryl.

In any and all embodiments, the substituents may be selected from a subset of the listed alternative items. For example, in some embodiments, R is selected from an optionally substituted or unsubstituted phenyl group, an optionally substituted or unsubstituted naphthyl group, an optionally substituted or unsubstituted pyridyl or quinolyl group; in further embodiments, R is selected from optionally substituted or unsubstituted phenyl.

In some embodiments, R is selected from an optionally substituted or unsubstituted phenyl group, an optionally substituted or unsubstituted naphthyl group, an optionally substituted or unsubstituted pyridyl or quinolyl group, and the hydrogen on R may be substituted by one or more $R^3$ groups, $R^3$ is selected from halogen, methyl, ethyl, propyl, isopropyl, tert-butyl, trifluoromethyl, methoxy, nitro, cyano. In still other embodiments, R is selected from an optionally substituted or unsubstituted phenyl group, the hydrogen on R may be substituted by one or more $R^3$ groups, and $R^3$ is selected halogen, methyl, ethyl, propyl, isopropyl, tert-butyl, trifluoromethyl, methoxy, nitro, cyano.

More specifically, the preferred compounds of the present invention are selected from any of the following compounds:

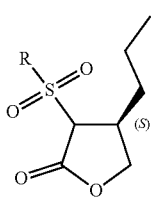

wherein, R is:

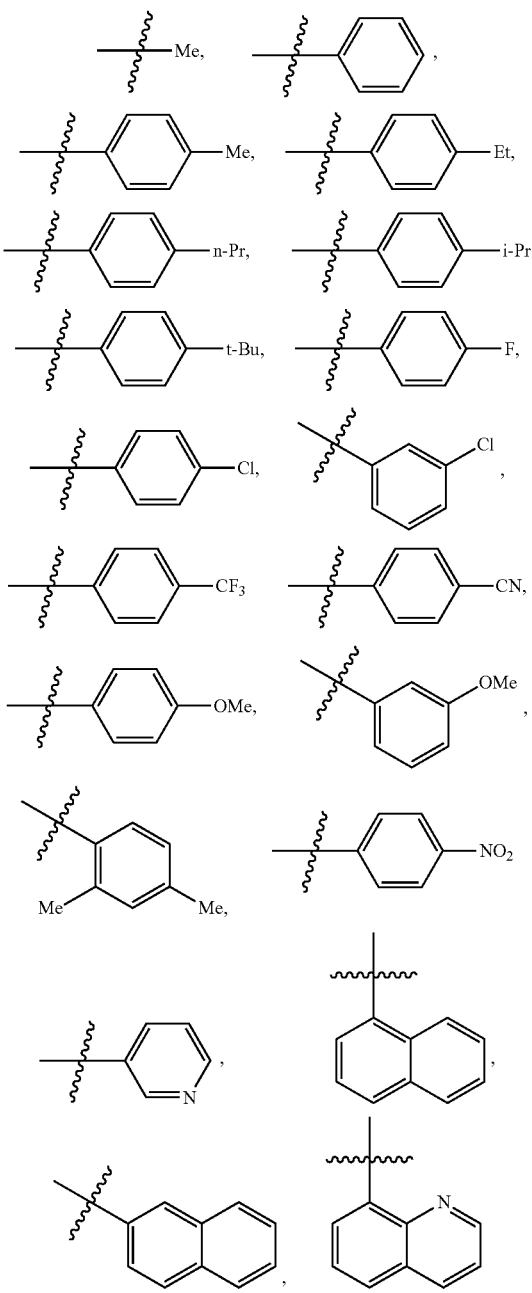

The present application provides a method for preparing the compounds of formula III, which includes the following steps:

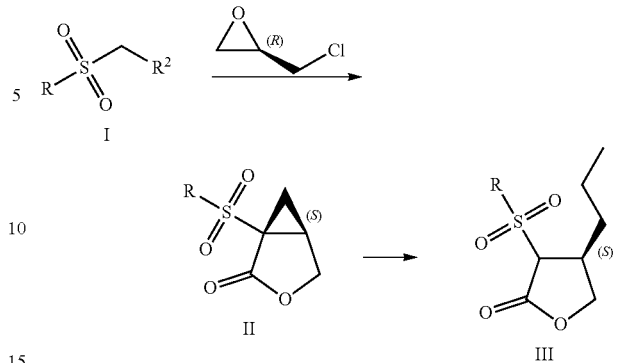

Wherein, R is selected from optionally substituted or unsubstituted $C_1$-$C_5$ alkyl, optionally substituted or unsubstituted $C_6$-$C_{12}$ aryl or optionally substituted or unsubstituted 5-12 membered heteroaryl; $R^2$ is selected from cyano or ester group.

In some embodiments, R is selected from optionally substituted or unsubstituted $C_1$-$C_5$ alkyl, optionally substituted or unsubstituted $C_6$-$C_{12}$ aryl, or optionally substituted or unsubstituted 5-12 membered heteroaryl; $R^2$ is selected from cyano, $C(O)OCH_3$, $C(O)OCH_2CH_3$ or $C(O)OC(CH_3)_3$. In further embodiments, R is selected from optionally substituted or unsubstituted $C_1$-$C_5$ alkyl, optionally substituted or unsubstituted $C_6$-$C_{12}$ aryl or optionally substituted or unsubstituted 5-12 membered heteroaryl, and $R^2$ is selected from cyano.

In some embodiments, R is selected from optionally substituted or unsubstituted phenyl, optionally substituted or unsubstituted naphthyl or optionally substituted or unsubstituted pyridyl or quinolyl; $R^2$ is selected from cyano, $C(O)OCH_3$, $C(O)OCH_2CH_3$ or $C(O)OC(CH_3)_3$. In further embodiments, R is selected from optionally substituted or unsubstituted phenyl, optionally substituted or unsubstituted naphthyl or optionally substituted or unsubstituted pyridyl or quinolyl, and $R^2$ is selected from cyano.

In some embodiments, R is selected from optionally substituted or unsubstituted phenyl; $R^2$ is selected from cyano, $C(O)OCH_3$, $C(O)OCH_2CH_3$ or $C(O)OC(CH_3)_3$. In further embodiments, R is selected from optionally substituted or unsubstituted phenyl; and $R^2$ is selected from cyano.

In some embodiments, R is selected from optionally substituted or unsubstituted phenyl, optionally substituted or unsubstituted naphthyl or optionally substituted or unsubstituted pyridyl or quinolyl, the hydrogens on R may be substituted by one or more $R^3$ groups, and $R^3$ is selected from halogen, methyl, ethyl, propyl, isopropyl, tert-butyl, trifluoromethyl, methoxy, nitro, cyano; $R^2$ is selected from cyano, $C(O)OCH_3$, $C(O)OCH_2CH_3$ or $C(O)OC(CH_3)_3$. In further embodiments, R is selected from optionally substituted or unsubstituted phenyl, optionally substituted or unsubstituted naphthyl or optionally substituted or unsubstituted pyridyl or quinolyl, the hydrogens on R may be substituted by one or more $R^3$ groups, and $R^3$ is selected from halogen, methyl, ethyl, propyl, isopropyl, tert-butyl, trifluoromethyl, methoxy, nitro, cyano; and $R^2$ is selected from cyano.

In some embodiments, R is selected from optionally substituted or unsubstituted phenyl, the hydrogens on R may be substituted by one or more $R^3$ groups, and $R^3$ is selected from halogen, methyl, ethyl, propyl, isopropyl, tert-butyl, trifluoromethyl, methoxy, nitro, cyano; $R^2$ is selected from cyano, C(O)OCH$_3$, C(O)OCH$_2$CH$_3$ or C(O)OC(CH$_3$)$_3$. In further embodiments, R is selected from optionally substituted or unsubstituted phenyl, the hydrogens on R may be substituted by one or more R$^3$ groups, and R$^3$ is selected from halogen, methyl, ethyl, propyl, isopropyl, tert-butyl, trifluoromethyl, methoxy, nitro, cyano; and R$^2$ is selected from cyano.

More specifically, a preferred compound for the preparation of III in the present invention, wherein R is selected from any one of the following compounds:

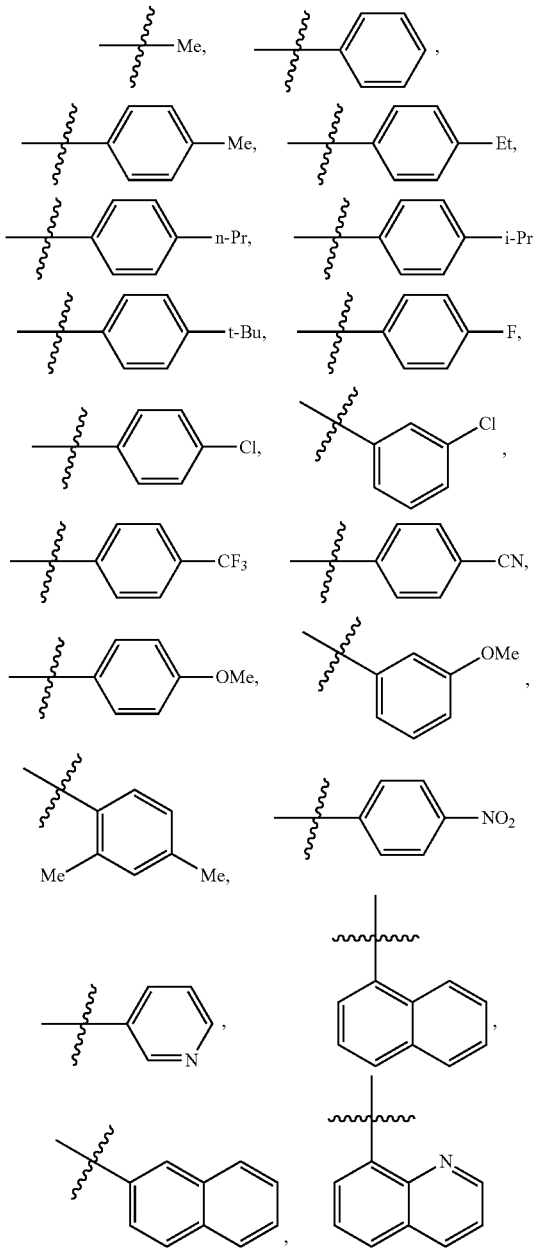

R$^2$ is selected from cyano, C(O)OCH$_3$, C(O)OCH$_2$CH$_3$ or C(O)OC(CH$_3$)$_3$, and preferred selected from cyano. In some specific embodiments, the synthesis method of the corresponding preferred compounds III includes the following step:

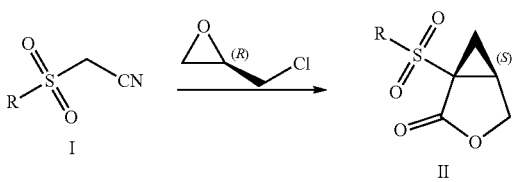

In other specific embodiments, the synthesis method of the corresponding preferred compounds III includes the following step:

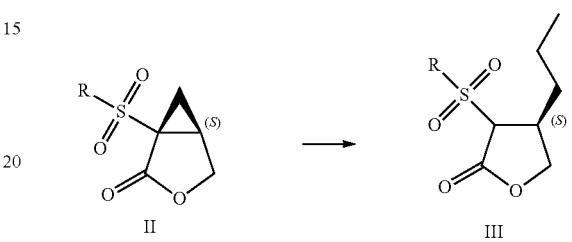

More specifically, in some specific embodiments, the synthesis method of the corresponding preferred compounds III includes the following steps:

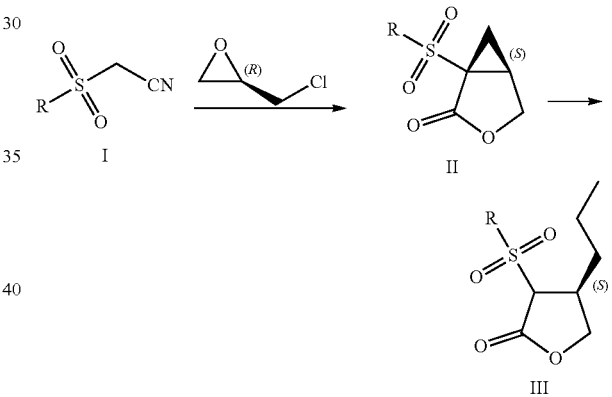

It will also be understood by those skilled in the field that, according to the synthetic route described above, those skilled in the field can obtain the desired products by reasonably selecting the raw materials and synthetic methods known in the field according to their technical knowledge and conventional technical means.

In a specific embodiment, the reaction conditions of each reaction step may be:

Preparation of the Compound of Formula II from the Compound of Formula I

The compound of the formula I is reacted with R-epichlorohydrin in a solvent under the action of a base (a), followed by treatment with an acid or a base (b) to prepare the compound of the formula II.

More specifically, in some embodiments, the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate.

In some embodiments, the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the acid is selected from one or more of acetic acid, propionic acid, citric acid, hydrochloric acid, sulfuric acid, phosphoric acid, nitric acid, methanesulfonic acid, benzenesulfonic acid or p-toluenesulfonic acid.

In some further embodiments, the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the acid is selected from one or more of acetic acid, propionic acid, hydrochloric acid or sulfuric acid.

In still further embodiments, In some further embodiments, the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the acid is selected from one or more of acetic acid, propionic acid, hydrochloric acid or sulfuric acid; the base (b) is selected from one or more of sodium hydroxide, potassium hydroxide, potassium carbonate or sodium carbonate.

In still further embodiments, the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the acid is selected from one or more of acetic acid, propionic acid, hydrochloric acid or sulfuric acid; the base (b) is selected from one or more of sodium hydroxide, potassium hydroxide, potassium carbonate or sodium carbonate; the solvent is selected from one or more of water, methanol, ethanol, propanol, isopropanol, tert-butanol, n-butanol, tetrahydrofuran, methyltetrahydrofuran, acetonitrile, toluene, dimethyl sulfoxide, N,N-dimethylformamide, N,N-dimethylacetamide or N-methylpyrrolidone.

In some preferred specific embodiments, the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the equivalent of alkali (a) is between 1 and 10; the acid is selected from one or more of acetic acid, propionic acid, hydrochloric acid or sulfuric acid; the base (b) is selected from one or more of sodium hydroxide, potassium hydroxide, potassium carbonate or sodium carbonate; the solvent is selected from one or more of water, methanol, ethanol, propanol, isopropanol, tert-butanol, n-butanol, tetrahydrofuran, methyltetrahydrofuran, acetonitrile, toluene, dimethyl sulfoxide, N,N-dimethylformamide, N,N-dimethylacetamide or N-methylpyrrolidone.

In some preferred specific embodiments, the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the equivalent of alkali (a) is between 1 and 10; the equivalent of R-epichlorohydrin is between 0.1 and 5; the acid is selected from one or more of acetic acid, propionic acid, hydrochloric acid or sulfuric acid; the base (b) is selected from one or more of sodium hydroxide, potassium hydroxide, potassium carbonate or sodium carbonate; the solvent is selected from one or more of water, methanol, ethanol, propanol, isopropanol, tert-butanol, n-butanol, tetrahydrofuran, methyltetrahydrofuran, acetonitrile, toluene, dimethyl sulfoxide, N,N-dimethylformamide, N,N-dimethylacetamide or N-methylpyrrolidone.

In some more specific embodiments, a preferred compound of formula II is prepared from a compound of formula I:

The compound of the formula I is reacted with R-epichlorohydrin in a solvent under the action of a base (a), followed by treatment with an acid or a base (b) to prepare the compound of the formula II, wherein the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the equivalent of alkali (a) is between 1 and 10; the equivalent of R-epichlorohydrin is between 0.1 and 5; the solvent is selected from one or more of water, methanol, ethanol, propanol, isopropanol, tert-butanol, n-butanol, tetrahydrofuran, methyltetrahydrofuran, acetonitrile, toluene, dimethyl sulfoxide, N,N-dimethylformamide; the acid is selected from one or more of acetic acid, propionic acid, hydrochloric acid or sulfuric acid; and the base (b) is selected from one or more of sodium hydroxide, potassium hydroxide, potassium carbonate or sodium carbonate.

Preparation of the Compound of Formula III from the Compound of Formula II

The compound of formula III is prepared by reacting a compound of formula II with an ethyl metal reagent in an aprotic organic solvent.

In some embodiments, the ethyl metal reagent is selected from ethyl magnesium bromide, ethyl magnesium chloride, diethyl zinc, ethyl lithium or diethyl lead.

In some further embodiments, the ethyl metal reagent includes ethyl magnesium bromide, ethyl magnesium chloride, diethyl zinc, ethyl lithium or diethyl lead; the ethyl metal reagent is used in combination with cuprous iodide, cuprous cyanide or anhydrous zinc chloride.

In still further embodiments, the ethyl metal reagent is selected from ethyl magnesium bromide, ethyl magnesium chloride, diethyl zinc, ethyl lithium or diethyl lead; the ethyl metal reagent is used in combination with cuprous iodide, cuprous cyanide or anhydrous zinc chloride; the aprotic organic solvent is selected from tetrahydrofuran (THF), methyltetrahydrofuran, toluene, dichloromethane, diethyl ether or methyl tert-butyl ether.

In still further embodiments, the ethyl metal reagent is selected from ethyl magnesium bromide, ethyl magnesium chloride, diethyl zinc, ethyl lithium or diethyl lead, and used in a molar equivalent weight between 1 and 5; the ethyl metal reagent is used in combination with cuprous iodide, cuprous cyanide or anhydrous zinc chloride; the aprotic organic solvent is selected from tetrahydrofuran (THF), methyltetrahydrofuran, toluene, dichloromethane, diethyl ether or methyl tert-butyl ether.

In some more specific embodiments, the ethyl metal reagent is selected from ethyl magnesium bromide, ethyl magnesium chloride, diethyl zinc, ethyl lithium or diethyl lead, and used in a molar equivalent weight between 1 and 5; the ethyl metal reagent is used in combination with cuprous iodide, cuprous cyanide or anhydrous zinc chloride, and used in a molar equivalent weight of between 0.01 and 2; the aprotic organic solvent is selected from tetrahydrofuran (THF), methyltetrahydrofuran, toluene, dichloromethane, diethyl ether or methyl tert-butyl ether.

In further specific embodiments, the preferred compound for III is prepared from compound II.

The compound of the formula III is prepared by reacting a compound of the formula II with an ethyl metal reagent which is used in combination with cuprous iodide, cuprous cyanide or anhydrous zinc chloride in an aprotic organic solvent; wherein the aprotic organic solvent is selected from tetrahydrofuran (THF), methyltetrahydrofuran, toluene, dichloromethane, diethyl ether or methyl tert-butyl ether; ethyl metal reagents include ethyl magnesium bromide, ethyl magnesium chloride, diethyl zinc, ethyl lithium or diethyl lead, the molar equivalents are used between 1 and 5; and the molar equivalents of cuprous iodide, cuprous cyanide or anhydrous zinc chloride are between 0.01 and 2.

The compound of formula III can be used to prepare the key intermediate of Brivaracetam as described in the formula IV, and the reaction route is as follows:

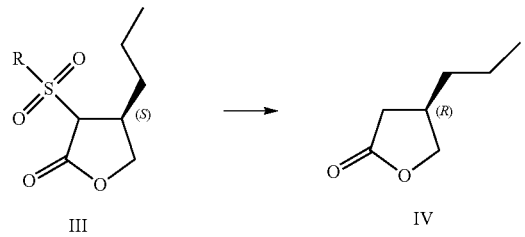

In a specific embodiment, the reaction conditions of this reaction step may be that the compound of formula IV is prepared by removing the sulfonyl group of the compound of formula III by a reducing agent in an organic solvent.

In some embodiment, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water.

In some further embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from active metals and salts thereof, tin hydride or transition metals.

In still further embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from Mg, Ca, Al, Zn, Ni, Sm, SmI$_2$.

In some specific embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from active metals and salts thereof, tin hydride or transition metals; the reducing agent is used in combination with one or more of Hg, I$_2$, Lewis acid or base.

In some further specific embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from Mg, Ca, Al, Zn, Ni, Sm, SmI$_2$; the reducing agent is used in combination with one or more of Hg, I$_2$, Lewis acid or base.

In some further specific embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from active metals and salts thereof, tin hydride or transition metals; the reducing agent is used in combination with one or more of Hg, I$_2$, Lewis acid or base, wherein the Lewis acid is selected from hydrochloric acid, ammonium chloride, trimethylchlorosilane, titanium tetrachloride, nickel chloride, nickel bromide, nickel iodide, acetic acid, and propionic acid, methanesulfonic acid, p-toluenesulfonic acid, benzenesulfonic acid, citric acid, etc.

In some further specific embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from Mg, Ca, Al, Zn, Ni, Sm, SmI$_2$; the reducing agent is used in combination with one or more of Hg, I$_2$, Lewis acid or base, wherein the Lewis acid is selected from hydrochloric acid, ammonium chloride, trimethylchlorosilane, titanium tetrachloride, nickel chloride, nickel bromide, nickel iodide, acetic acid, and propionic acid, methanesulfonic acid, p-toluenesulfonic acid, benzenesulfonic acid, citric acid, etc.

In some further specific embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from active metals and salts thereof, tin hydride or transition metals; the reducing agent is used in combination with one or more of Hg, I$_2$, Lewis acid or base, wherein the Lewis acid is selected from hydrochloric acid, ammonium chloride, trimethylchlorosilane, titanium tetrachloride, nickel chloride, nickel bromide, nickel iodide, acetic acid, propionic acid, methanesulfonic acid, p-toluenesulfonic acid, benzenesulfonic acid, citric acid, etc, and wherein the Lewis base comprises ammonia, methylmagnesium bromide, tetramethylethylenediamine, sodium acetate, potassium acetate, etc.

In some further specific embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from Mg, Ca, Al, Zn, Ni, Sm, SmI$_2$; the reducing agent is used in combination with one or more of Hg, I$_2$, Lewis acid or base, wherein the Lewis acid is selected from hydrochloric acid, ammonium chloride, trimethylchlorosilane, titanium tetrachloride, nickel chloride, nickel bromide, nickel iodide, acetic acid, propionic acid, methanesulfonic acid, p-toluenesulfonic acid, benzenesulfonic acid, citric acid, etc, and wherein the Lewis base comprises ammonia, methylmagnesium bromide, tetramethylethylenediamine, sodium acetate, potassium acetate, etc.

In some further specific embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from active metals and salts thereof, tin hydride or transition metals, and used in a molar equivalent of between 1 and 30; the reducing agent is used in combination with one or more of Hg, $I_2$, Lewis acid or base, wherein the Lewis acid is selected from hydrochloric acid, ammonium chloride, trimethylchlorosilane, titanium tetrachloride, nickel chloride, nickel bromide, nickel iodide, acetic acid, propionic acid, methanesulfonic acid, p-toluenesulfonic acid, benzenesulfonic acid, citric acid, etc, and wherein the Lewis base comprises ammonia, methylmagnesium bromide, tetramethylethylenediamine, sodium acetate, potassium acetate, etc.

In some further specific embodiments, the organic solvent is selected from one or more of methanol, ethanol, isopropanol, N,N-dimethylformamide, N,N-dimethylacetamide, N-methylpyrrolidone, tetrahydrofuran and acetonitrile, or a mixed solvent with water; the reducing agent is selected from Mg, Ca, Al, Zn, Ni, Sm, $SmI_2$, and used in a molar equivalent of between 1 and 30; the reducing agent is used in combination with one or more of Hg, $I_2$, Lewis acid or base, wherein the Lewis acid is selected from hydrochloric acid, ammonium chloride, trimethylchlorosilane, titanium tetrachloride, nickel chloride, nickel bromide, nickel iodide, acetic acid, propionic acid, methanesulfonic acid, p-toluenesulfonic acid, benzenesulfonic acid, citric acid, etc, and wherein the Lewis base comprises ammonia, methylmagnesium bromide, tetramethylethylenediamine, sodium acetate, potassium acetate, etc.

More specifically, in some preferred embodiments, Formula IV is prepared from a compound of Formula III:

The compound of formula IV is prepared by removing the sulfonyl group of the compound of formula III by a reducing agent in an organic solvent, wherein the organic solvent is selected from one or more of methanol, ethanol, isopropanol, N,N-dimethylformamide, N,N-dimethylacetamide, N-methyl pyrrolidone, tetrahydrofuran, acetonitrile, or a mixed solvent with water; the reducing agent is Mg, which uses a molar equivalent of between 1 and 30, and the reducing agent is used in combination with one or more of hydrochloric acid and trimethyl chlorosilane, nickel chloride, nickel bromide, nickel iodide, acetic acid, propionic acid, methylmagnesium bromide, tetramethylethylenediamine, sodium acetate or potassium acetate.

More specifically, in some more preferred embodiments, Formula IV is prepared from a preferred compound of Formula III:

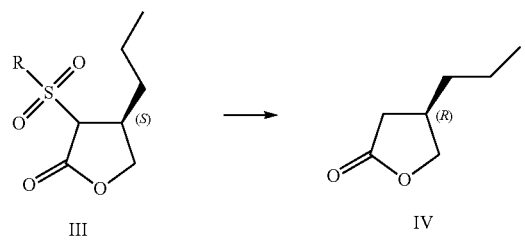

III → IV

The compound of formula IV is prepared by removing a sulfonyl group on a compound of formula III by a reducing agent in an organic solvent; wherein the organic solvent is selected from one or more of methanol, ethanol, isopropanol, N,N-dimethylformamide, N,N-dimethylacetamide, N-methylpyrrolidone, tetrahydrofuran, acetonitrile, or a mixed solvent with water; the reducing agent is Mg, which uses a molar equivalent of between 1 and 30, and the reducing agent is used in combination with one or more of hydrochloric acid, trimethylchlorosilane, nickel chloride, nickel bromide, nickel iodide, acetic acid, propionic acid, methyl magnesium bromide, tetramethylethylenediamine, sodium acetate or potassium acetate.

By the above scheme, the present invention has the following advantages compared with the prior art: the present invention provides a preparation method of 3-sulfonyl-substituted 4-propyl-dihydrofuran-2-one, and is used for synthesizing Brivaracetam intermediate (R)-4-propyl-dihydrofuran-2-one and APIs. The method has the advantages of short synthetic route, easy availability of raw materials, crystallization of intermediates, simple overall process and strong operability, and is suitable for industrial production.

DEFINITIONS

Unless otherwise stated, the following terms used in the specification and claims have the meanings discussed below. Variables defined in this section, such as A, R, X, Z and the like, are for reference within this section only, and are not meant to have the save meaning as may be used outside of this definitions section. Further, many of the groups defined herein can be optionally substituted. The listing in this definitions section of typical substituents is exemplary and is not intended to limit the substituents defined elsewhere within this specification and claims.

"–$\xi$–" represents the position of the substituent.

"$C_m$-$C_n$" refers to the carbon atoms contained in m-n.

"Alkyl" refers to a saturated aliphatic hydrocarbon radical or linker including straight chain and branched chain groups of 1 to 20 carbon atoms, preferably 1 to 12 carbon atoms, more preferably 1 to 8 carbon atoms, or 1 to 6 carbon atoms, or 1 to 4 carbon atoms. "Lower alkyl" refers specifically to an alkyl group with 1 to 4 carbon atoms. Examples of alkyl groups include —$(CH_2)_3$—, methyl, ethyl, propyl, 2-propyl, n-butyl, iso-butyl, tert-butyl, pentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring.

"Aryl" refers to an all-carbon monocyclic or fused-ring polycyclic groups of 6 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, Ocarbamyl, N-carbamyl, O-thiocarbamyl, N-thiocarbamyl, C-amido, N-amido, sulfinyl, sulfonyl, amino and —$NR^xR^y$, with $R^x$ and $R^y$ as defined above.

"Heteroaryl" refers to a monocyclic or fused ring group of 5 to 12 ring atoms containing one, two, three or four ring heteroatoms selected from N, O, and S, the remaining ring atoms being C, and, in addition, having a completely conjugated π-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —NR$^x$R$^y$ with R$^x$ and R$^y$ as defined above.

"Cyano" refers to a —C≡N group.

"Nitro" refers to a —NO$_2$ group.

"Ester" refers to a —C(O)OR" group with R" as defined herein except that R" cannot be hydrogen.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

As used herein, when any variable occurs more than one time in a chemical formula, its definition on each occurrence is independent of its definition at every other occurrence. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula III include, but are not limited to optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula III include Z- and E-forms (or cis- and trans-forms) of compounds with double bonds. Where compounds of Formula I exist in various tautomeric forms, chemical entities of the present invention include all tautomeric forms of the compound.

EXAMPLES

The invention includes, but is not limited to, the following examples to further illustrate the preparation of the compounds described herein.

The following embodiments are only used to illustrate the specific embodiments of the invention, which can enable the professional and technical personnel to understand the invention more comprehensively, but can not limit the invention in any way. In the specific embodiments of the present invention, the technical means or methods not specifically described are conventional technical means or methods in the technical field, etc.

The chemical reagents used in the following examples are all commercially available chemical reagents.

In an exemplary embodiment of the present invention, the synthesis of formula III and the route for preparing the key intermediate (R)-4-propyl-dihydrofuran-2-one of Brivaracetam are as follows:

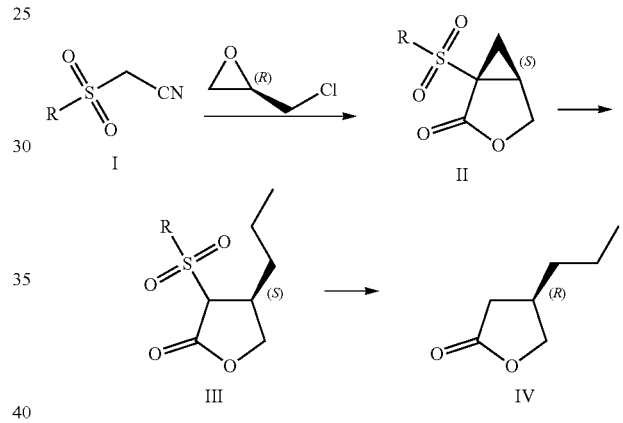

In the above synthetic routes, those skilled in the field may also make changes to the above synthetic routes, such as changing specific reaction conditions as required or adjusting the synthetic routes of one or more steps, which are not separated from the essential contents of the present invention and are within the scope of protection of the present application.

Example 1 Preparation of Compound II

To a 100 mL three-necked flask with mechanical stirring was added compound I (5.1 mmol) and 30 mL of methanol at room temperature. Sodium methoxide (1.10 g, 20.4 mmol) was added portionwise. The resulting mixture was heated to 35-40° C. and stirred for 10 minutes. Then the temperature was cooled to 20-25° C., and R-epichlorohydrin (0.71 g, 0.97 mmol) was added and the addition was completed in about 10 minutes. The internal temperature rose to 50-55° C. and stirred for 4 h. A mixture of 5 mL of water and 5 mL of acetic acid was added to the reaction mixture and stirred for another 15 h. The reaction mixture was diluted with 20 mL of water, and extracted with dichloromethane (30 mL*2). The combined organic phases was washed with a saturated NaHCO$_3$ solution (15 mL*2), and dried over anhydrous sodium sulfate. Most of the solvent was removed under reduced pressure, and the residue was purified by recrystallization with ethanol or by column chromatography to give compound II as shown in Table 1.

TABLE 1

| Comp. No. | Structure | Name | MS [M + 1] |
|---|---|---|---|
| II-1 | 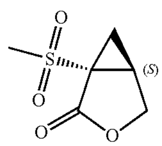 | (1R,5S)-1-(methylsulfonyl)-3-oxabicyclo[3.1.0]hexan-2-one | 177 |
| II-2 | 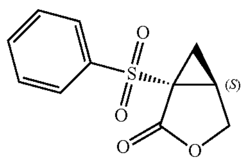 | (1R,5S)-1-(phenylsulfonyl)-3-oxabicyclo[3.1.0]hexan-2-one | 239 |
| II-3 | 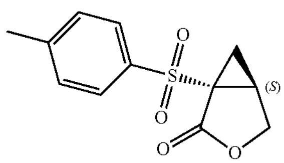 | (1R,5S)-1-tosyl-3-oxabicyclo[3.1.0]hexan-2-one | 253 |
| II-4 | 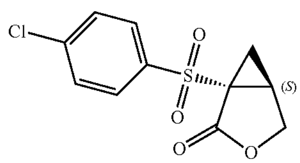 | (1R,5S)-1-((4-chlorophenyl)sulfonyl)-3-oxabicyclo[3.1.0]hexan-2-one | 273 |
| II-5 | 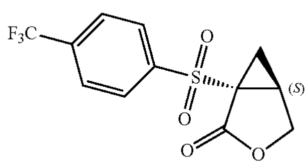 | (1R,5S)-1-((4-(trifluoromethyl)phenyl)sulfonyl)-3-oxabicyclo[3.1.0]hexan-2-one | 307 |
| II-6 | 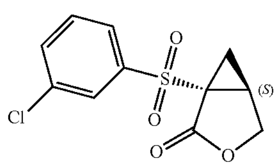 | (1R,5S)-1-((3-chlorophenyl)sulfonyl)-3-oxabicyclo[3.1.0]hexan-2-one | 273 |
| II-7 | 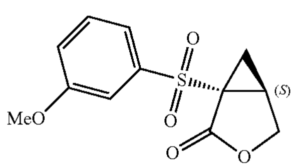 | (1R,5S)-1-((3-methoxyphenyl)sulfonyl)-3-oxabicyclo[3.1.0]hexan-2-one | 269 |
| II-8 | 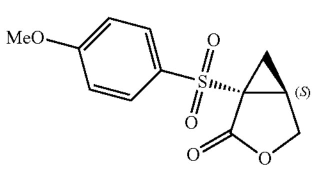 | (1R,5S)-1-((4-methoxyphenyl)sulfonyl)-3-oxabicyclo[3.1.0]hexan-2-one | 269 |
| II-9 | 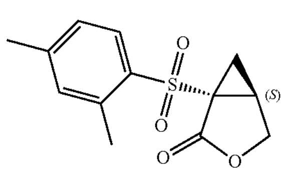 | (1R,5S)-1-((2,4-dimethylphenyl)sulfonyl)-3-oxabicyclo[3.1.0]hexan-2-one | 267 |

TABLE 1-continued

| Comp. No. | Structure | Name | MS [M + 1] |
|---|---|---|---|
| II-10 | 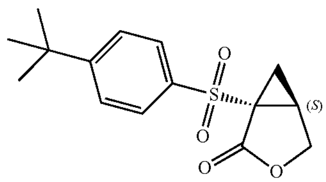 | (1R,5S)-1-((4-(tert-butyl)phenyl)sulfonyl)-3-oxabicyclo[3.1.0]hexan-2-one | 295 |
| II-11 | 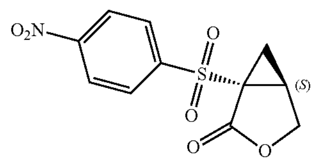 | (1R,5S)-1-((4-nitrophenyl)sulfonyl)-3-oxabicyclo[3.1.0]hexan-2-one | 284 |
| II-12 | 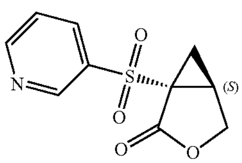 | (1R,5S)-1-(pyridin-3-ylsulfonyl)-3-oxabicyclo[3.1.0]hexan-2-one | 240 |
| II-13 | 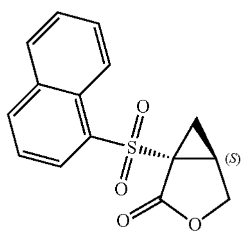 | (1R,5S)-1-(naphthalen-1-ylsulfonyl)-3-oxabicyclo[3.1.0]hexan-2-one | 289 |
| II-14 | 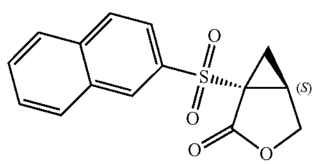 | (1R,5S)-1-(naphthalen-2-ylsulfonyl)-3-oxabicyclo[3.1.0]hexan-2-one | 289 |
| II-15 | 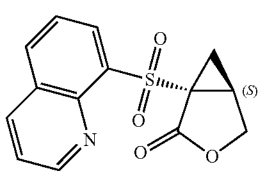 | (1R,5S)-1-(quinolin-8-ylsulfonyl)-3-oxabicyclo[3.1.0]hexan-2-one | 290 |
| II-16 | 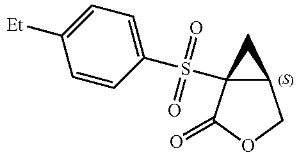 | (1R,5S)-1-((4-ethylphenyl)sulfonyl)-3-oxabicyclo[3.1.0]hexan-2-one | 267 |
| II-17 | 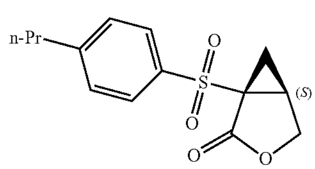 | (1R,5S)-1-((4-propylphenyl)sulfonyl)-3-oxabicyclo[3.1.0]hexan-2-one | 281 |

TABLE 1-continued

| Comp. No. | Structure | Name | MS [M + 1] |
|---|---|---|---|
| II-18 | i-Pr-phenyl sulfonyl oxabicyclohexanone (S) | (1R,5S)-1-((4-isopropyl-phenyl)sulfonyl)-3-oxabicyclo[3.1.0]hexan-2-one | 281 |
| II-19 | F-phenyl sulfonyl oxabicyclohexanone (S) | (1R,5S)-1-((4-fluoro-phenyl)sulfonyl)-3-oxabicyclo[3.1.0]hexan-2-one | 257 |
| II-20 | NC-phenyl sulfonyl oxabicyclohexanone (S) | 4-(((1R,5S)-2-oxo-3-oxabicyclo[3.1.0]hexan-1-yl)sulfonyl)benzonitrile | 264 |

Example 2 Preparation of Compound III

To a 100 mL three-necked flask with mechanical stirring was added THF (10 mL) and CuI (224 mg, 1.18 mmol). Cooled to −45° C.-50° C., and Ethyl magnesium chloride solution (2.1 mL, 4.2 mmol) was added dropwise over 1 h. The resulting mixture was warmed to −5° C. and continued to stirred for 1 h. Then a solution of compound II (1.49 mmol) in THF (5 mL) was added dropwise over 45 min and the temperature was retained at −5~-10° C. during the addition. The reaction mixture was added saturated aqueous ammonium chloride solution (5 mL) and MTBE (5 mL) after reacting for 15 min. The resulting mixture was stirred for another 2.5 h. The organic phase was collected and the aqueous phase was extracted with 10 mL MTBE again. The combined organic phases was washed with water (10 mL*2) and brine (10 mL), then dried with anhydrous Na₂SO₄. The solid was filtered off by suction, and the filtrate was concentrated. The residue was added an appropriate amount of ethanol, mixed and concentrated again. The crude was purified by stirring in ethanol or by column chromatography. Dried under vacuum to constant weight gives compound III as shown in Table 2.

TABLE 2

| Comp. No. | Structure | Name | MS [M + 1] |
|---|---|---|---|
| III-1 | methylsulfonyl propyl dihydrofuranone (S) | (4S)-3-(methyl-sulfonyl)-4-propyldihydro-furan-2(3H)-one | 207 |
| III-2 | phenylsulfonyl propyl dihydrofuranone (S) | (4S)-3-(phenyl-sulfonyl)-4-propyldihydro-furan-2(3H)-one | 269 |
| III-3 | tosyl propyl dihydrofuranone (S) | (4S)-4-propyl-3-tosyldihydro-furan-2(3H)-one | 283 |
| III-4 | 4-chlorophenylsulfonyl propyl dihydrofuranone (S) | (4S)-3-((4-chloro-phenyl)sulfonyl)-4-propyldihydro-furan-2(3H)-one | 303 |

TABLE 2-continued

| Comp. No. | Structure | Name | MS [M + 1] |
|---|---|---|---|
| III-5 | F₃C-phenyl-SO₂-(propyl)dihydrofuran-2(3H)-one | (4S)-4-propyl-3-((4-(trifluoromethyl)phenyl)sulfonyl)dihydrofuran-2(3H)-one | 337 |
| III-6 | 3-Cl-phenyl-SO₂-(propyl)dihydrofuran-2(3H)-one | (4S)-3-((3-chlorophenyl)sulfonyl)-4-propyldihydrofuran-2(3H)-one | 303 |
| III-7 | 3-MeO-phenyl-SO₂-(propyl)dihydrofuran-2(3H)-one | (4S)-3-((3-methoxyphenyl)sulfonyl)-4-propyldihydrofuran-2(3H)-one | 299 |
| III-8 | 4-MeO-phenyl-SO₂-(propyl)dihydrofuran-2(3H)-one | (4S)-3-((4-methoxyphenyl)sulfonyl)-4-propyldihydrofuran-2(3H)-one | 299 |
| III-9 | 2,4-dimethylphenyl-SO₂-(propyl)dihydrofuran-2(3H)-one | (4S)-3-((2,4-dimethylphenyl)sulfonyl)-4-propyldihydrofuran-2(3H)-one | 297 |
| III-10 | 4-tert-butyl-phenyl-SO₂-(propyl)dihydrofuran-2(3H)-one | (4S)-3-((4-(tert-butyl)phenyl)sulfonyl)-4-propyldihydrofuran-2(3H)-one | 325 |
| III-11 | 4-O₂N-phenyl-SO₂-(propyl)dihydrofuran-2(3H)-one | (4S)-3-((4-nitrophenyl)sulfonyl)-4-propyldihydrofuran-2(3H)-one | 314 |
| III-12 | pyridin-3-yl-SO₂-(propyl)dihydrofuran-2(3H)-one | (4S)-4-propyl-3-(pyridin-3-ylsulfonyl)dihydrofuran-2(3H)-one | 270 |
| III-13 | naphthalen-1-yl-SO₂-(propyl)dihydrofuran-2(3H)-one | (4S)-3-(naphthalen-1-ylsulfonyl)-4-propyldihydrofuran-2(3H)-one | 319 |
| III-14 | naphthalen-2-yl-SO₂-(propyl)dihydrofuran-2(3H)-one | (4S)-3-(naphthalen-2-ylsulfonyl)-4-propyldihydrofuran-2(3H)-one | 319 |
| III-15 | quinolin-8-yl-SO₂-(propyl)dihydrofuran-2(3H)-one | (4S)-4-propyl-3-(quinolin-8-ylsulfonyl)dihydrofuran-2(3H)-one | 320 |
| III-16 | 4-Et-phenyl-SO₂-(propyl)dihydrofuran-2(3H)-one | (4S)-3-((4-ethylphenyl)sulfonyl)-4-propyldihydrofuran-2(3H)-one | 297 |

TABLE 2-continued

| Comp. No. | Structure | Name | MS [M + 1] |
|---|---|---|---|
| III-17 | n-Pr, phenyl sulfonyl dihydrofuran-2(3H)-one, (S) | (4S)-4-propyl-3-((4-propyl-phenyl)sul-fonyl)dihydro-furan-2(3H)-one | 311 |
| III-18 | i-Pr, phenyl sulfonyl dihydrofuran-2(3H)-one, (S) | (4S)-3-((4-iso-propylphenyl)sul-fonyl)-4-propyldihydro-furan-2(3H)-one | 311 |
| III-19 | F, phenyl sulfonyl dihydrofuran-2(3H)-one, (S) | (4S)-3-((4-fluoro-phenyl)sulfonyl)-4-propyldihydro-furan-2(3H)-one | 287 |
| III-20 | NC, phenyl sulfonyl tetrahydrofuran, (S) | 4-(((4S)-2-oxo-4-propyltetra-hydrofuran-3-yl)sul-fonyl)benzo-nitrile | 294 |

Example 3 Preparation of Compound II-2

To the mixture of toluene/water (v/v, 5/5 mL) in the reaction flask was added (Phenylsulfonyl)acetonitrile (500 mg, 2.8 mmol), NaOH (276 mg, 6.9 mmol) and Tetrabutylammonium hydrogen sulfate (50 mg). After stirring for 15 min, R-epichlorohydrin (381 mg, 4.1 mmol) was added into the mixture. The resulting mixture was stirred at 100° C. for 1 h, then was added 1 mL of conc. HCl (aq.) and continued to stir for 3 h. The reaction mixture was diluted with DCM (10 mL), and the organic phase was collected, dried and concentrated. The residue was purified by column chromatography to give white solid, Yield: 25.7%.

Example 4 Preparation of Compound II-2

To a 5.0 L three-necked flask with mechanical stirring function was added (Phenylsulfonyl)acetonitrile (92.4 g, 0.51 mol) and sodium ethoxide (436.0 g, 20% ethanol solution), and the mixture was stirred at 15 to 20° C. for 30 minutes. R-epichlorohydrin (70.7 g, 0.97 mol) was added dropwise, and the addition was completed in about 10 minutes. The internal temperature was raised to 50-55° C., and the mixture was reacted for about 1 h, then concentrated. To the residue was added MTBE (1.0 L), water (0.5 L), and NaOH (51 g), and the mixture was stirred for 1 h. The aqueous phase was collected, and acidified to pH~1 with conc. HCl (aq.), then stirred at 50° C. for 15 h. The aqueous phase was extracted with MTBE (300 mL*3). The combined organic phases were washed once with saturated sodium bicarbonate (0.5 L) and water (0.5 L) respectively and concentrated. The residue was crystallized with 400 mL of ethanol, filtered to give compound II-2 as a solid (56.7 g, yield: 46.7%).

Example 5 Preparation of Compound II-3

To a 2.0 L three-necked flask with mechanical stirring function was added 4-(Methylphenyl)sulfonylacetonitrile (100 g, 0.51 mol) and sodium ethoxide (436.0 g, 20% ethanol solution), and the mixture was stirred at 20° C. for 30 minutes. R-epichlorohydrin (70.7 g, 0.97 mol) was added dropwise, and the addition was completed in about 10 minutes. The internal temperature was raised to 50-55° C., and the mixture was reacted for about 1 h, then concentrated. To the residue was added MTBE (1.0 L), water (0.5 L), and NaOH (51 g), and the mixture was stirred for 1 h. The aqueous phase was collected, and acidified to pH~1 with conc. HCl (aq.), then stirred at 50° C. for 6 h. The aqueous phase was extracted with MTBE (300 mL*3). The combined organic phases were washed once with saturated sodium bicarbonate (0.5 L) and water (0.5 L) respectively and concentrated. The residue was crystallized with 400 mL of MeOH, filtered to give compound II-3 as a solid, yield: 50.2%.

Example 6 Preparation of Compound III-2

To a 2.0 L three-necked flask with mechanical stirring function was added THF (100 mL) and CuI (22.4 g, 117.8 mmol). Cooled to −45° C.-50° C., and ethylmagnesium bromide (185 mL, 370.0 mmol) was added dropwise. The addition was completed in about 1 hour. The mixture was continued to stir for 1 h, then warmed to −15° C. To the mixture was added dropwise a solution of the compound II-2 (39.9 g) in THF (240 mL), and the addition was completed in about 1 h. The mixture was continued to stir at −15° C. for 2 h, then saturated NH$_4$Cl solution (400 mL) was added, followed by ethyl acetate (400 mL), and stirred for another 2 h. The mixture was allowed to stand, the organic phase was separated, and the aqueous phase was extracted with ethyl acetate (200 mL). The combined organic phase was washed with water (200 mL*2), brine (200 mL) respectively, dried over anhydrous sodium sulfate, filtered, and concentrated. The product was crystallized from isopropanol to give a white solid (27.4 g, Yield: 61.0%).

Example 7 Preparation of Compound III-3

To a 2.0 L three-necked flask with mechanical stirring function was added THF (100 mL) and CuCN (10.6 g, 117.8 mmol). Cooled to −45° C.-50° C., and ethylmagnesium bromide (185 mL, 370.0 mmol) was added dropwise in about 1 hour. After stirring for 1 h, a solution of the compound II-3 (42.2 g) in THF (240 mL) was added dropwise in about 1 h, and kept the temperature at −45° C.-50° C. during the addition. The mixture was warmed to −15° C. and stirred for 2 h. Then saturated NH$_4$Cl solution (400 mL) was added, followed by ethyl acetate (400 mL), and stirred for another 2 h. The mixture was allowed to stand, the organic phase was separated, and the aqueous phase was extracted with ethyl acetate (200 mL). The combined organic phase was washed with water (200 mL*2), brine (200 mL) respectively, dried over anhydrous sodium sulfate, filtered, and concentrated. The product was crystallized from isopropanol to give a white solid (23.8 g, Yield: 50.4%).

Example 8 Preparation of Compound III-3

To a 20.0 L reactor with mechanical stirring function was added THF (2.8 L) and CuI (152.4 g, 0.8 mol), and cooled to −45° C.-50° C., then ethylmagnesium bromide (2.0 L, 4.0 mol) was added dropwise in about 1 hour. After stirring for 1 h, a solution of the compound II-3 (400.0 g) in THF (3.2 L) was added dropwise in about 1 h, and kept the temperature at −45° C.-50° C. during the addition. The mixture was warmed to −5° C. and stirred for 2 h. Then saturated $NH_4Cl$ solution (4.0 L) was added, followed by MTBE (4.0 L), and stirred for another 2 h. The mixture was allowed to stand, the organic phase was separated, and the aqueous phase was extracted with MTBE (4.0 L). The combined organic phase was washed with water (2.0 L*2), brine (4.0 L) respectively, dried over anhydrous sodium sulfate, filtered, and concentrated. The product was crystallized from EtOH (1.5 L) to give a white solid (293.1 g, Yield: 65.5%).

Example 9 Preparation of Compound IV

To a 100 mL three-necked flask with mechanical stirring was added compound III-2 (2.68 g, 10.0 mmol), magnesium turnings (4.8 g, 200.0 mmol) and methanol (100 mL) under nitrogen atmosphere. The resulting mixture was warmed to 50° C. and stirred for 48 h, then poured into an aqueous hydrochloric acid solution, and extracted twice with DCM (100 mL*2). The collected phases were washed with water (100 mL*2) and saturated brine (100 mL), dried with anhydrous $Na_2SO_4$, and filtered. The filtrate was evaporated to dryness in vacuum to give a crude (1.21 g), which was distilled under reduced pressure to give a colorless oil (865 mg, 67.5%).

Example 10 Preparation of Compound IV

To a 100 mL three-necked flask with mechanical stirring was added compound III-3 (2.82 g, 10.0 mmol), magnesium turnings (2.4 g, 100.0 mmol) and methanol (100 mL) under nitrogen atmosphere. The resulting mixture was warmed to 50° C. and stirred for 48 h, then poured into an aqueous hydrochloric acid solution, and extracted twice with DCM (100 mL*2). The collected phases were washed with water (100 mL*2) and saturated brine (100 mL), dried with anhydrous $Na_2SO_4$, and filtered. The filtrate was evaporated to dryness in vacuum to give a crude (1.21 g), which was distilled under reduced pressure to give a colorless oil (720 mg, 56.6%).

Example 11 Preparation of Compound IV

To a 100 mL three-necked flask with mechanical stirring was added compound III-3 (2.82 g, 10.0 mmol), magnesium turnings (2.4 g, 100.0 mmol) and DMF (100 mL) under nitrogen atmosphere. The resulting mixture was warmed to 50° C. and stirred for 48 h, then poured into an aqueous hydrochloric acid solution, and extracted twice with DCM (100 mL*2). The collected phases were washed with water (100 mL*2) and saturated brine (100 mL), dried with anhydrous $Na_2SO_4$, and filtered. The filtrate was evaporated to dryness in vacuum to give a crude (1.18 g), which was distilled under reduced pressure to give a colorless oil (602 mg, 47.2%).

Example 12 Preparation of Compound IV

To a 100 mL three-necked flask with mechanical stirring was added compound III-3 (2.82 g, 10.0 mmol), magnesium turnings (2.4 g, 100.0 mmol) and DMF (100 mL) under nitrogen atmosphere, then TMSCl (0.2 mL) was added at room temperature. The resulting mixture was warmed to 50° C. and stirred for 24 h, then poured into an aqueous hydrochloric acid solution, and extracted twice with DCM (100 mL*2). The collected phases were washed with water (100 mL*2) and saturated brine (100 mL), dried with anhydrous $Na_2SO_4$, and filtered. The filtrate was evaporated to dryness in vacuum to give a crude (1.35 g), which was distilled under reduced pressure to give a colorless oil (845 mg, 66.0%).

Example 13 Preparation of Compound IV

To a 100 mL three-necked flask with mechanical stirring was added compound III-3 (2.82 g, 10.0 mmol), magnesium turnings (2.4 g, 100.0 mmol) and DMF (100 mL) under nitrogen atmosphere, then HCl (6N aq., 0.5 mL) was added at room temperature. The resulting mixture was warmed to 50° C. and stirred for 48 h, then poured into an aqueous hydrochloric acid solution, and extracted twice with DCM (100 mL*2). The collected phases were washed with water (100 mL*2) and saturated brine (100 mL), dried with anhydrous $Na_2SO_4$, and filtered. The filtrate was evaporated to dryness in vacuum to give a crude (1.28 g), which was distilled under reduced pressure to give a colorless oil (751 mg, 58.7%).

Example 14 Preparation of Compound IV

To a 2 L three-necked flask with mechanical stirring was added compound III-3 (56.4 g, 0.2 mol), activated magnesium turnings (48 g, 2.0 mol) and DMF (1.0 L) under nitrogen atmosphere, then HCl (6N aq., 0.5 mL) was added at room temperature. The resulting mixture was warmed to 50° C. and stirred for 48 h, then poured into an aqueous hydrochloric acid solution, and extracted twice with DCM (500 mL*2). The collected phases were washed with water (500 mL*2) and saturated brine (500 mL), dried with anhydrous $Na_2SO_4$, and filtered. The filtrate was evaporated to dryness in vacuum to give a crude (22.0 g), which was distilled under reduced pressure to give a colorless oil (15.5 g, 60.5%).

Although the present invention has been described in considerable detail with reference to certain preferred versions thereof, other versions are possible. Therefore, the spirit and scope of the present invention should not be limited to the description of the preferred versions described herein. All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the invention, in addition to those described herein, will be apparent to those skilled in the art from the foregoing description. Such modifications are also intended to fall within the scope of the appended claims. Each reference cited in the present application is herein incorporated by reference in its entirety.

What is claimed is:

1. A compound having the structure of formula III:

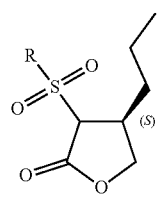

III wherein, R represents $C_1$-$C_5$ alkyl, $C_6$-$C_{12}$ aryl, or 5-12 membered heteroaryl, wherein R is optionally substituted by one or more groups selected from halogen, methyl, ethyl, propyl, isopropyl, t-butyl, trifluoromethyl, methoxy, nitro or cyano.

2. The compound of claim 1, wherein the compound is selected from:

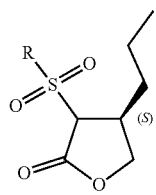

wherein, R is

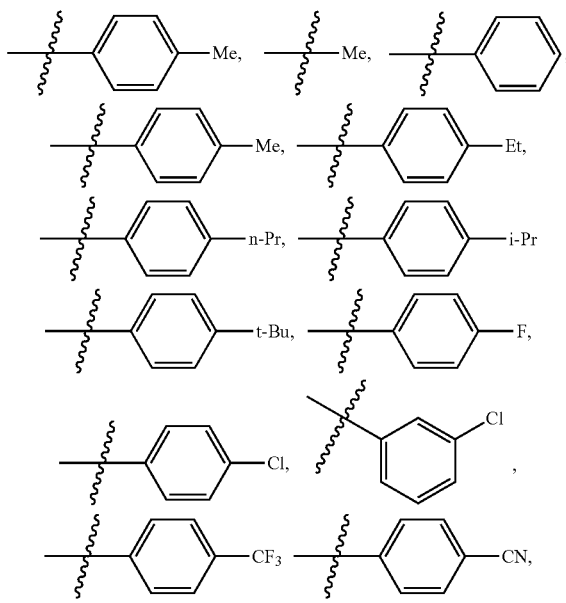

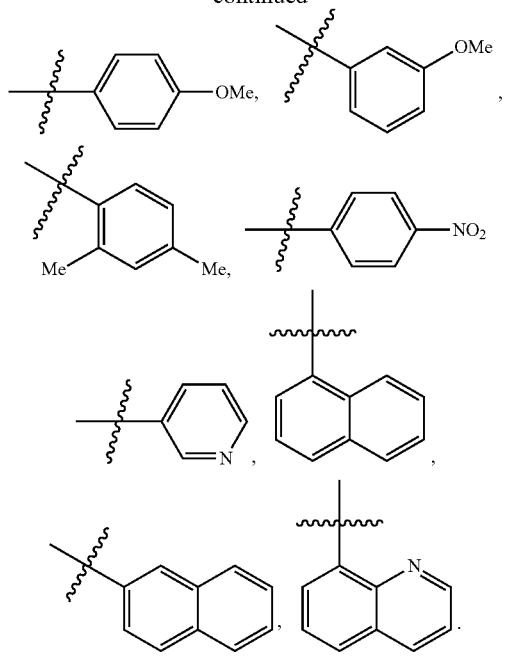

3. A method for the preparation of the compounds of claim 2, comprising the step of:

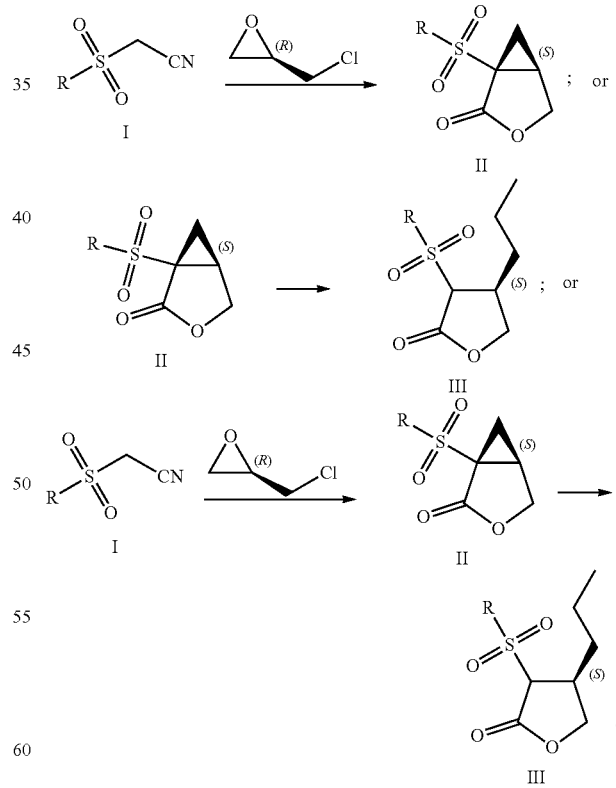

4. The method according to claim 3, when the method comprises preparation of the compound of formula II from the compound of formula I, the method comprises the following steps:

reacting the compound of the formula I with R-epichlorohydrin in a solvent under the action of a base (a), followed by treatment with an acid or a base (b) to prepare the compound of the formula II.

5. The method according to claim 4, wherein the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the acid is selected from one or more of acetic acid, propionic acid, citric acid, hydrochloric acid, sulfuric acid, phosphoric acid, nitric acid, methanesulfonic acid, benzenesulfonic acid or p-toluenesulfonic acid; the base (b) is selected from one or more of sodium hydroxide, potassium hydroxide, potassium carbonate or sodium carbonate.

6. The method according to claim 4, wherein the solvent is selected from one or more of water, methanol, ethanol, propanol, isopropanol, tert-butanol, n-butanol, tetrahydrofuran, methyltetrahydrofuran, acetonitrile, toluene, dimethyl sulfoxide, N,N-dimethylformamide, N,N-dimethylacetamide or N-methylpyrrolidone.

7. The method according to claim 3, wherein when the method comprises preparation of the compound of formula II from the compound of formula I, the method comprises the following steps:
reacting the compound of the formula I with R-epichlorohydrin in a solvent under the action of a base (a), followed by treatment with an acid or a base (b) to prepare the compound of the formula II, wherein the base (a) is selected from one or more of sodium methoxide, potassium methoxide, magnesium methoxide, sodium ethoxide, potassium ethoxide, sodium t-butoxide, potassium t-butoxide, sodium hydroxide, potassium hydroxide, potassium carbonate, sodium carbonate or cesium carbonate; the equivalent of alkali (a) is between 1 and 10; the equivalent of R-epichlorohydrin is between 0.1 and 5; the solvent is selected from one or more of water, methanol, ethanol, propanol, isopropanol, tert-butanol, n-butanol, tetrahydrofuran, methyltetrahydrofuran, acetonitrile, toluene, dimethyl sulfoxide, N,N-dimethylformamide; the acid is selected from one or more of acetic acid, propionic acid, hydrochloric acid or sulfuric acid; and the base (b) is selected from one or more of sodium hydroxide, potassium hydroxide, potassium carbonate or sodium carbonate.

8. The method according to claim 3,
when the method comprises preparation of the compound of formula III from the compound of formula II, the method comprises the following steps:
preparing the compound of formula III by reacting a compound of formula II with an ethyl metal reagent in an aprotic organic solvent.

9. The method according to claim 8, wherein the ethyl metal reagent includes ethyl magnesium bromide, ethyl magnesium chloride, diethyl zinc, ethyl lithium or diethyl lead.

10. The method according to claim 9, wherein the ethyl metal reagent is used in combination with cuprous iodide, cuprous cyanide or anhydrous zinc chloride.

11. The method according to claim 10, wherein the aprotic organic solvent is selected from tetrahydrofuran (THF), methyltetrahydrofuran, toluene, dichloromethane, diethyl ether or methyl tert-butyl ether.

12. The method according to claim 3, when the method comprises preparation of the compound of formula III from the compound of formula II, the method comprises the following steps:
in an aprotic organic solvent, reacting the compound of formula II with ethyl metal reagents which is used in combination with cuprous iodide, cuprous cyanide or anhydrous zinc chloride to prepare the compound of III; wherein the aprotic organic solvent is selected from tetrahydrofuran (THF), methyltetrahydrofuran, toluene, dichloromethane, diethyl ether or methyl tert-butyl ether; the ethyl metal reagent include ethyl magnesium bromide, ethyl magnesium chloride, diethyl zinc, ethyl lithium or diethyl lead, which is used in molar equivalents between 1-5; and the molar equivalent of cuprous iodide, cuprous cyanide or anhydrous zinc chloride is between 0.01 and 2.

13. A method for preparing a compound of formula IV of Brivaracetam intermediate using the compound according to claim 1, comprising the step of

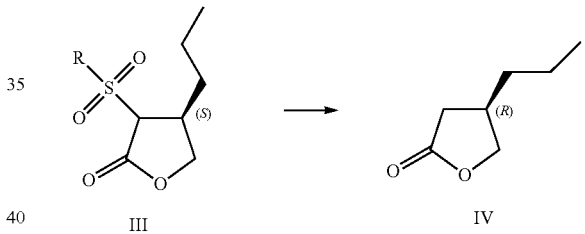

preparing the compound of formula IV by removing a sulfonyl group on the compound of formula III by a reducing agent in an organic solvent; wherein the organic solvent is selected from one or more of methanol, ethanol, isopropanol, N,N-dimethylformamide, N,N-dimethylacetamide, N-methylpyrrolidone, tetrahydrofuran, acetonitrile, or a mixed solvent with water; the reducing agent is Mg, which is used in a molar equivalent of between 1 and 30, and the reducing agent is used in combination with one or more of hydrochloric acid, trimethylchlorosilane, nickel chloride, nickel bromide, nickel iodide, acetic acid, propionic acid, methyl magnesium bromide, tetramethylethylenediamine, sodium acetate or potassium acetate.

* * * * *